Figure 1:
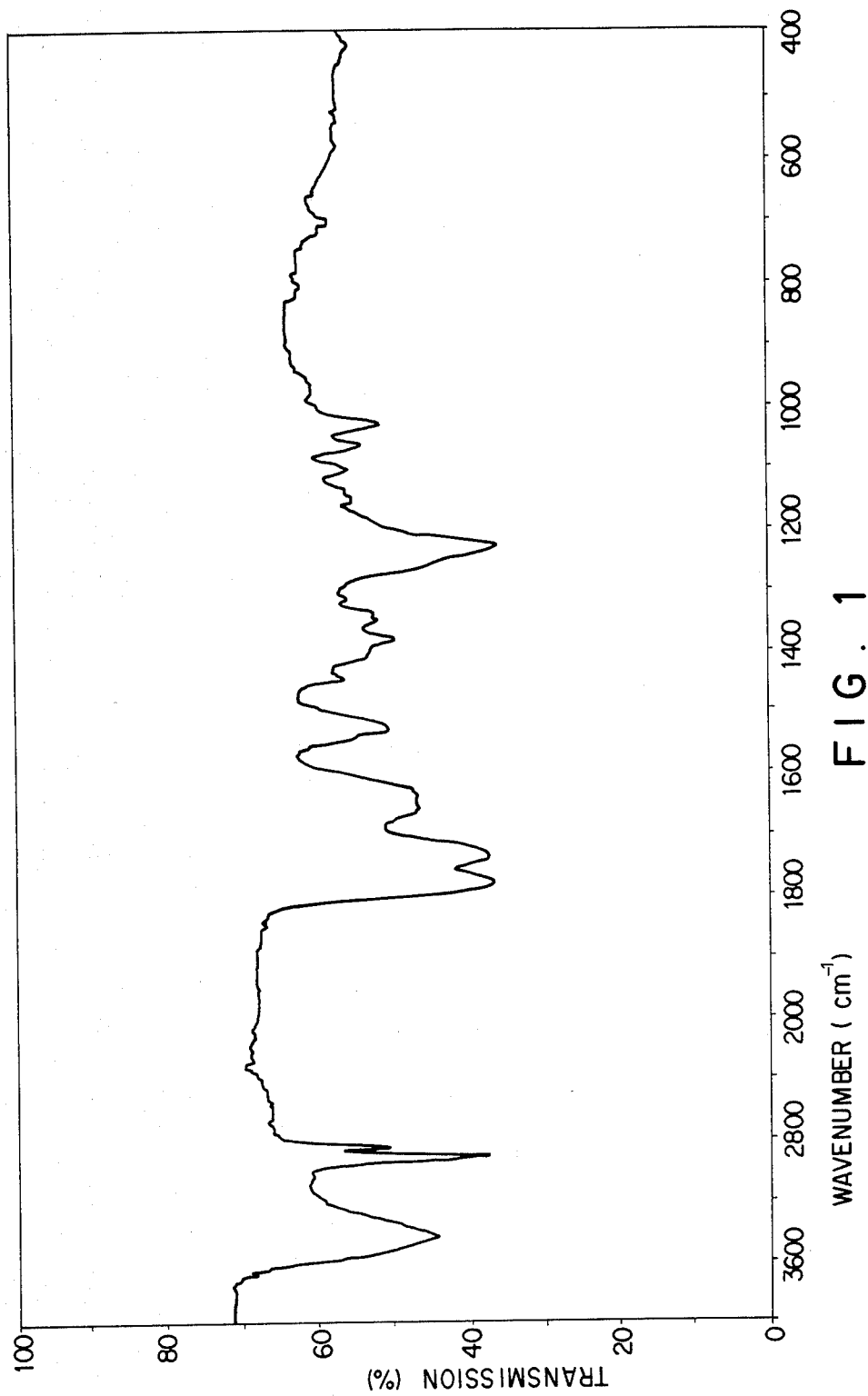

United States Patent [19]

Muto et al.

[11] Patent Number: 4,496,561

[45] Date of Patent: Jan. 29, 1985

[54] CEPHALOSPORIN DERIVATIVE

[75] Inventors: Shigeaki Muto, Tokyo; Kouichi Niimura, Sayama; Takao Ando, Tokyo; Akihiko Kanno, Tokyo; Takao Furusho, Machida; Chikao Yoshikumi, Kunitachi, all of Japan

[73] Assignee: Kureha Kagaku Kogyo Kabushiki Kaisha, Tokyo, Japan

[21] Appl. No.: 418,762

[22] Filed: Sep. 16, 1982

[30] Foreign Application Priority Data

Sep. 22, 1981 [JP] Japan ................................. 56-149870

[51] Int. Cl.$^3$ .................. C07D 501/20; A61K 31/545
[52] U.S. Cl. ..................................... 514/209; 544/030; 544/021; 544/023
[58] Field of Search ....................... 544/30, 28, 27, 21, 544/23; 424/246

[56] References Cited

U.S. PATENT DOCUMENTS 3,167,550  1/1965  Chow et al. ........................ 544/30
3,252,973  5/1966  Flynn ............................. 260/239.1
3,923,798 12/1975  Horii et al. ....................... 544/30

Primary Examiner—Nicholas S. Rizzo

[57] ABSTRACT

A cephalosporin derivative having an antibacterial activity similar to a cephalosporin antibiotic in living bodies without affecting the intestinal bacterial colonies, a method for preparing the derivative and a pharmaceutical composition in a dosage unit form containing the derivative as an active ingredient are disclosed.

8 Claims, 5 Drawing Figures

CEPHALOSPORIN DERIVATIVE

The present invention relates to a compound derived from a cephalosporin and to a medicine containing the compound as an active ingredient. In particular, the present invention relates to a compound obtained by chemically modifying a cephalosporin, an antibacterial activity of the compound being lost by such a chemical modification but recovered when the compound is absorbed into a living body, and to a medicine containing the compound as an active ingredient and exhibiting a cephalosporin-like activity in the living body.

Cephalosporins are well known as excellent antibiotics due to the selective toxicity to bacteria. However, the cephalosporin antibiotic has a serious defect, that is, it may disturb the beneficial bacterial colonies ordinarily present in living bodies, particularly the intestinal bacterial colonies, since it may be also antibacterially active against the beneficial bacteria. This defect is very serious when such an antibiotic is orally administered. As a result, "microbisme selectionné et substitué" is caused resulting in colities and diarrhea.

It is an object of the present invention to provide an antibiotic without having the defect.

An another object of the present invention is to provide a compound which is useful as an active ingredient of the antibacterial medicine.

A still another object of the present invention is to provide a medicine exhibiting an antibacterial activity similar to a cephalosporin antibiotic in living body.

A compound of the present invention (hereinafter referred to as the present compound) is derived from a cephalosporin and has the general formula (I):

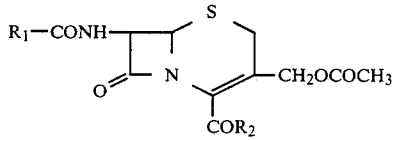
(I)

wherein $R_1$ is

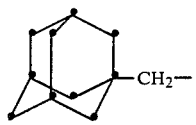

group, and $R_2$ is $-OR_3$ wherein $R_3$ is a hydrogen atom, an alkyl group having 1 to 4 carbon atoms or an alkali metal;

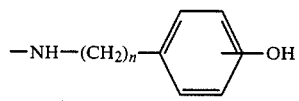

wherein n is 0, 1 or 2; or

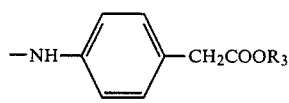

wherein $R_3$ is the same meaning as above. The present compound may be in a form other than alkali metal salt, for example, alkali earth metal salt, aluminum salt, ammonium salt. And the present compound may have a lactone ring formed by combining $-COR_2$ and $-CH_2OCOCH_3$ groups.

The present compound is derived from a cephalosporin antibiotic by a chemical modification. It is absorbed into a living body without affecting the bacterial colonies ordinarily present in living bodies and shows an antibacterial activity only when entering into blood, therefore, the present compound is an antibiotic of the new type quite different from the conventional cephalosporin antibiotics.

The present compound may be synthesized by the following process.

7-Aminocephalosporanic acid having the general formula (II):

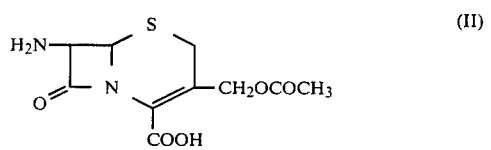
(II)

or an alkyl ester or salt thereof is added into an acetone solution of acid chloride of the formula (III)

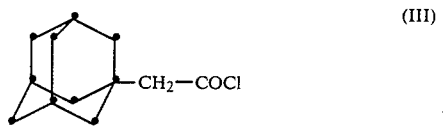
(III)

drop by drop in a mixed solvent of water and acetone in the presence of alkali metal. The whole system is brought into reaction for 0.5 to 48 hours at a temperature of $-30°$ to $+40°$ C. After the reaction is over, the present compound is collected by the conventional method such as extraction with a solvent, washing with a solvent and recrystallization.

The thus-obtained present compound wherein $R_2$ is $-OR_3$ is dissolved in an organic solvent, for example, benzene, tetrahydrofuran, dimethylformamide, chloroform, pyridine, dicyclohexylamine, acetone, triethylamine, chloromethane, dioxane, methanol, ethanol, water, ether and the like. It is preferable to add an activating agent such as carbodiimide, ethyl chloroformate, oxalyl chloride and the like. Then into the thus-prepared solution, an amine compound having the general formula (IV):

$$NH_2-R_4 \quad\quad (IV)$$

wherein $R_4$ is  or

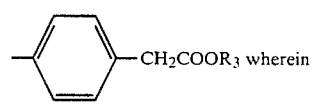

n and $R_3$ are the same meaning as above, is added. The whole system is brought into reaction at the temperature of $-30°$ to $+50°$ C. for 0.5 to 48 hours. After the reaction is over, the present compound is collected by the conventional method such as extraction with a solvent, washing with a solvent, recrystallization and the like.

The thus-obtained product is further treated in a mixed solvent of dioxane and 2N-hydrochloric acid solution while shaking to obtain the present compound having a lactone ring.

As seen from Examples described below, the present compound has low toxicity and exhibits an antibacterial activity in a living body without affecting the intestinal bacterial colonies.

The present compound can be useful in the same field as the conventional cephalosporin antibiotics since the present compound is transformed into a cephalosporin antibiotic in a living body.

The present compound can be used in a dosage unit from such as a drug or a pharmaceutical composition. The composition may contain 0.01 to 99.5% by weight, generally 0.1 to 90% by weight of the present compound as an active ingredient.

The pharmaceutical composition may contain a pharmaceutically acceptable carrier, diluent or adjuvant as well as at least one of the present compound. Further, the composition may contain filler, extender, binder, wetting agent, disintegrant, retarder of dissolution, accelerator of reabsorption, adhesive carrier and/or lubricant, for example, starch, mannitol, silicic acid, cellulose derivative, gelatin, alginate, glycerol, agar, calcium carbonate, sodium hydrogen carbonate, paraffin, quatarnary ammonium compound, glycerol monostearate, kaolin, bentonite, talc, potassium stearate, polyethylene glycol and the like.

The pharmaceutical composition may be administered orally or rectally or by injection. The dosage form for oral administration may be tablet, capsule, powder, granule, pill, ampoule or the like. The composition may be also in the form of pharmaceutically acceptable emulsion, solution, suspension and the like.

A syrup or elixir may contain an inert diluent such as water and paraffin and may be used as a liquid composition suitable for oral administration. These composition may contain an adjuvant such as wetting agent, edulcorant and seasoning agent.

A suppository containing the present compound as an active ingredient may contain polyethylene glycol and/or fatty acid or ester thereof.

The pharmaceutical composition for injection may be a sterilized aqueous or nonaqueous solution, suspension or emulsion and may contain, for example, propylene glycol, polyethylene glycol, olive oil and the like.

The present compound may be useful for the same as the conventional cephalosporin antibiotics and effective in treating an infectious disease due to bacteria such as Streptococcus, Pneumococcus, Gonococcus, diphteria bacillus, Staphylococcus, Spirochaeta, Actinomyces, Shigella, E. coli, Myxomycetes, Entereococcus, Meningococcus and the like. The diseases to be able to be treated with the present compound is exemplified as follows; tonsil; pharyngitis, laryngitis, wound, burn, postoperative secondary infection, lymphadenitis, septicemia, bacterial endocarditis, pneumonia, pulmonary suppuration, bronchitis, scarlet fever, gonorrhea, cystitis, pyothorax, urethritis, bacterial dysentery, meningitis, diphtheria, otitis media, carbuncle, actinomycosis and the like.

The dose of the drug or the pharmaceutical composition of the present compound may depend on the degree of the infection and the condition of the patient, and generally the dose of 0.1 to 10 g may be administered to an adult patient per one day, divided into several times.

The invention is illustrated in more detail in Examples which are not considering as limiting. It is apparent that many modifications and variations of the present invention may be made without departing from the spirit and scope thereof.

EXAMPLE 1

Synthesis of the compound represented by the following formula:

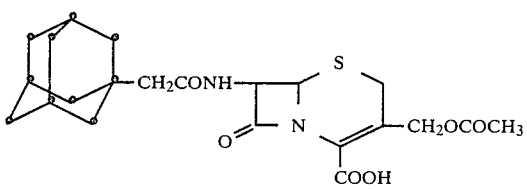

Into a solution of 2.72 g of 7-aminocephalosporanic acid and 1.68 g of sodium hydrogen carbonate in a mixed solvent of 30 ml of water and 20 ml of acetone, a solution of 2.13 g of 1-adamantaneacetyl chloride in 5 ml of acetone was added drop by drop while stirring into the mixed solvent at 0° C. After stirring the reaction mixture for one hour at 0° C. and further stirring for one hour at room temperature, it was left for a night at room temperature, and then the pH of the reaction mixture was adjusted to 4 by 1N-hydrochloric acid to educe the thus formed crystals. The crystal was extracted with 200 ml of ethyl acetate, and after washing the extract two times with water and drying on anhydrous magnesium sulfate, the solvent was distilled off from the dried extract. Recrystallizing the residue from a mixed solvent of ethyl acetate and n-hexane, 2.77 g of white powder, 7-(adamantane-1-acetamido)cephalosproranic acid, was obtained with a yield of 62%.

The characteristics of the present compound thus obtained were as follows:
(1) melting point; 201°-204° C.,
(2) elementary analysis;

|  | C (%) | H (%) | N (%) |
| --- | --- | --- | --- |
| theoretical: | 59.19 | 6.28 | 6.28 |
| experimental: | 59.11 | 6.29 | 6.18 |

(3) infrared absorption bands (KBr method); shown in FIG. 1.

EXAMPLE 2

Synthesis of the compound represented by the following formula:

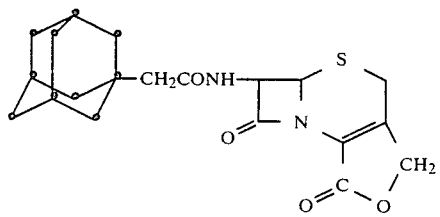

A solution of 3.88 g of 7-(adamantane-1-acetamido)-cephalosporanic acid in a mixed solvent of 50 ml of aqueous 2N-hydrochloric acid solution and 50 ml of dioxane was stirred for 16 hours at room temperature. The thus formed crystals were collected by filtration, washed two times with water. Recrystallizing the residue from a mixture of acetonitrile and dimethylformamide (5:1 by volume), 1.18 g of acicular crystals, 7-(adamantane-1-acetamido)cephalosporanolactone, were obtained with a yield of 61%.

The characteristics of the present compound thus obtained were as follows:
(1) melting point; 214°–215° C.,
(2) elementary analysis;

|  | C (%) | H (%) | N (%) |
|---|---|---|---|
| theoretical: | 61.86 | 6.19 | 7.22 |
| experimental: | 61.73 | 6.15 | 7.21 |

Figure 2:
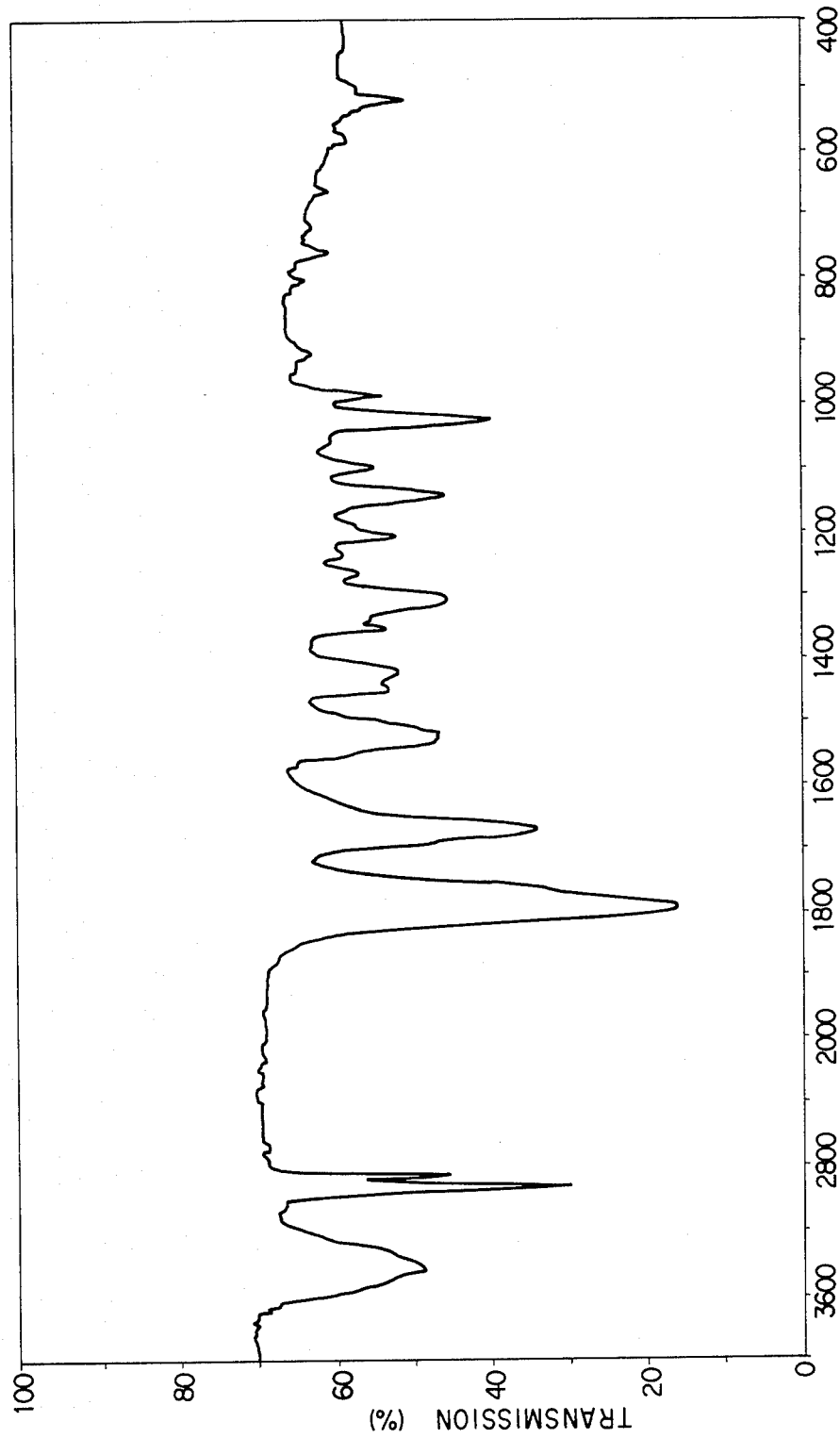

(3) infrared absorption bands (KBr method); shown in FIG. 2

EXAMPLE 3

Synthesis of the compound represented by the following formula;

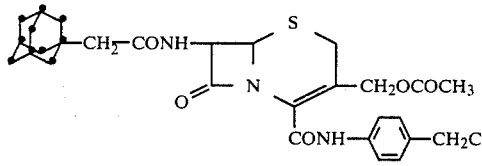

2.24 g of 7-(adamantane-1-acetamido)cephalosporanic acid, 0.83 g of methyl 4-aminophenylacetate and 1.05 g of N,N'-dicyclohexylcarbodiimide were dissolved into 30 ml of tetrahydrofuran. The thus-prepared solution was stirred at 25° C. for 24 hours. The crystals formed in the reaction mixture were filtered out and washed with 30 ml of tetrahydrofuran. Recrystallizing the residue from ethanol, 1.2 g of white powdery crystals, N-(4-hydroxyphenyl)-7-(adamantane-1-acetamido)cephalosporanoamide, were obtained with a yield of 40%.

The characteristics of the present compound thus obtained were as follows:
(1) melting point; 190°–192° C.,
(2) elementary analysis;

|  | C (%) | H (%) | N (%) |
|---|---|---|---|
| theoretical: | 62.52 | 6.22 | 7.06 |
| experimental: | 62.5 | 6.2 | 7.1 |

Figure 3:
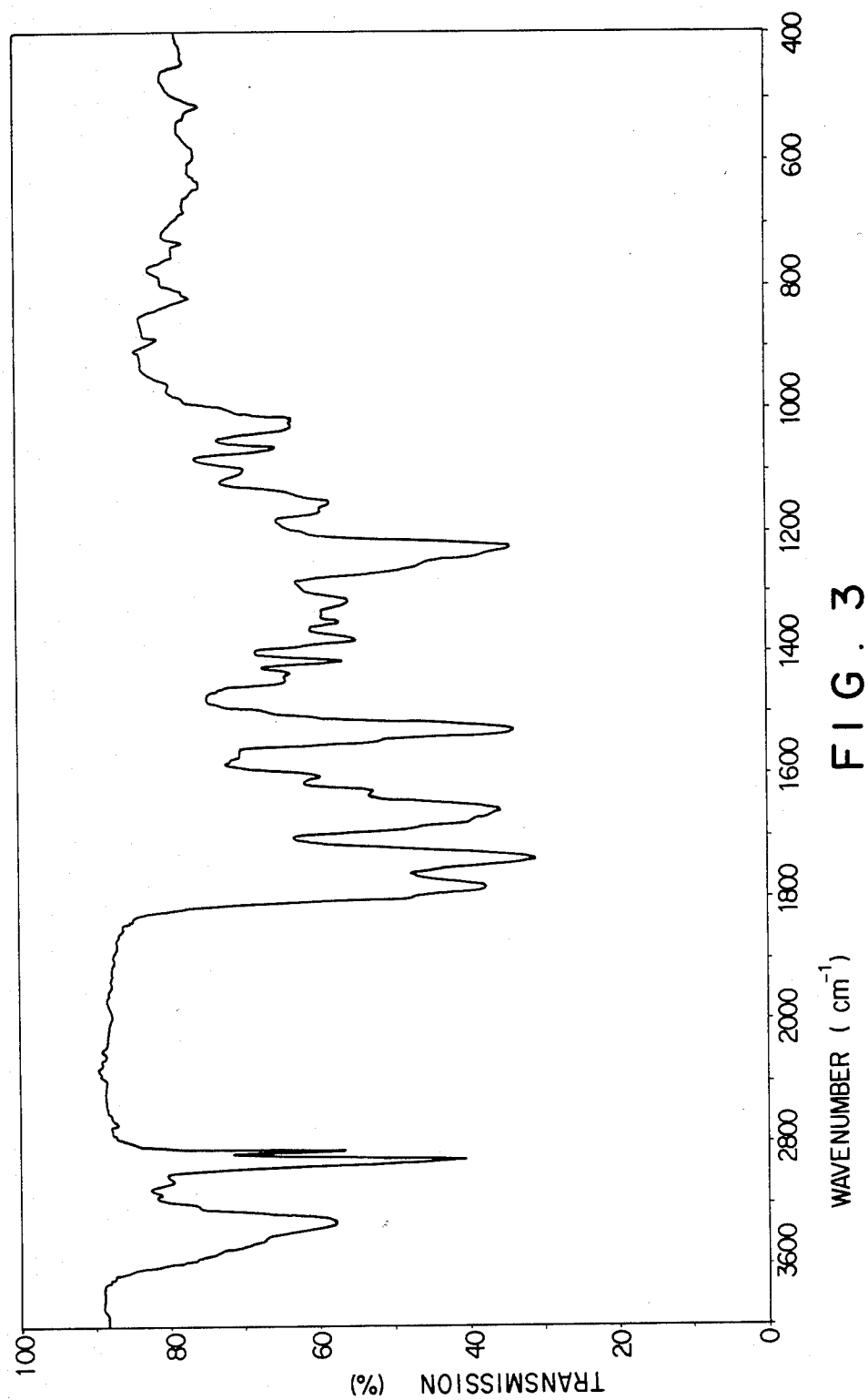

(3) infrared absorption bands (KBr method); $\nu_{max}$ (cm$^{-1}$): 2930, 1785, 1740, 1663, 1540, 1230 refer to FIG. 3.

(4) ultraviolet absorption bands in acetonitrile; $\lambda_{max}$ (nm): 223, 269.

EXAMPLE 4

Synthesis of the compound represented by the following formula;

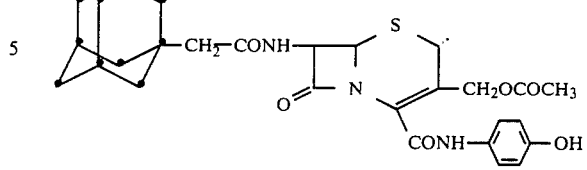

4.48 g of 7-(adamantane-1-acetamido)cephalosporanic acid, 1.09 g of 4-aminophenol and 2.10 g of N,N'-dicyclohexylcarbodiimide were dissolved into 60 ml of tetrahydrofuran. The thus-prepared solution was stirred at 15° C. for 24 hours. The crystals formed in the reaction mixture were filtered out and washed with 30 ml of tetrahydrofuran. Recrystallizing the residue from ethanol, 2.1 g of white powdery crystals, N-(4-hydroxyphenyl)-7-(adamantane-1-acetamido)cephalosporanoamide, were obtained with a yield of 39%.

The characteristics of the present compound thus obtained were as follows:
(1) melting point; 190°–191° C.,
(2) elementary analysis;

|  | C (%) | H (%) | N (%) |
|---|---|---|---|
| theoretical: | 62.52 | 6.22 | 7.06 |
| experimental: | 62.5 | 6.2 | 7.1 |

Figure 4:
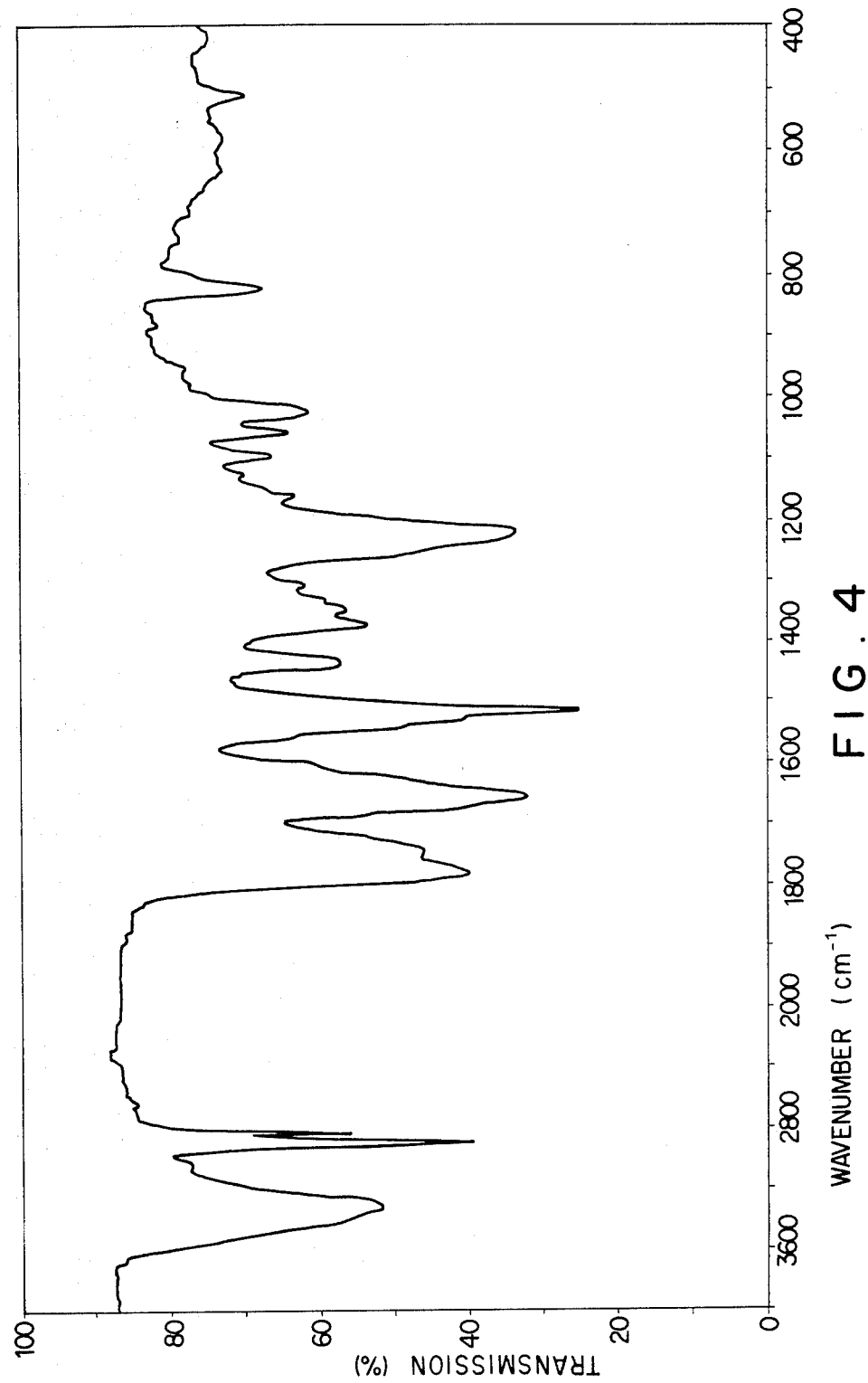

(3) infrared absorption bands (KBr method); $\nu_{max}$ (cm$^{-1}$): 2930, 1788, 1747, 1663, 1521, 1227. refer to FIG. 4.

(4) ultraviolet absorption bands in acetonitrile; $\lambda_{max}$ (nm): 237, 272.

EXAMPLE 5

Synthesis of the compound represented by the following formula;

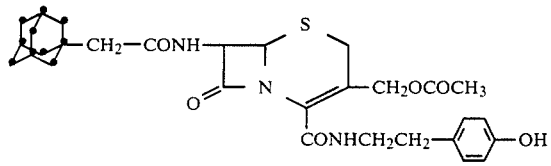

4.48 g of 7-(adamantane-1-acetamido)cephalosporanic acid, 1.37 g of quillamine and 2.10 g of N,N'-dicyclohexylcarbodiimide were dissolved into 70 ml of tetrahydrofuran. The thus-prepared solution was stirred at 10° C. for 34 hours. The crystals formed in the reaction mixture were filtered out and washed with 30 ml of tetrahydrofuran. Recrystallizing the residue from a mixed solvent of dimethylformamide and ethyl acetate, 2.9 g of pale-yellow powdery crystals, N-[beta-(4-hydroxyphenyl)ethyl]-7-(adamantane-1-acetamido)-cephalosporanoamide, were obtained with a yield of 51%.

The characteristics of the present compound thus obtained were as follows:
(1) melting point; 154°–156° C. (decomposition),
(2) elementary analysis;

|  | C (%) | H (%) | N (%) |
|---|---|---|---|
| theoretical: | 63.49 | 6.53 | 7.41 |

| | C (%) | H (%) | N (%) |
|---|---|---|---|
| experimental: | 63.6 | 6.5 | 7.4 |

Figure 5:
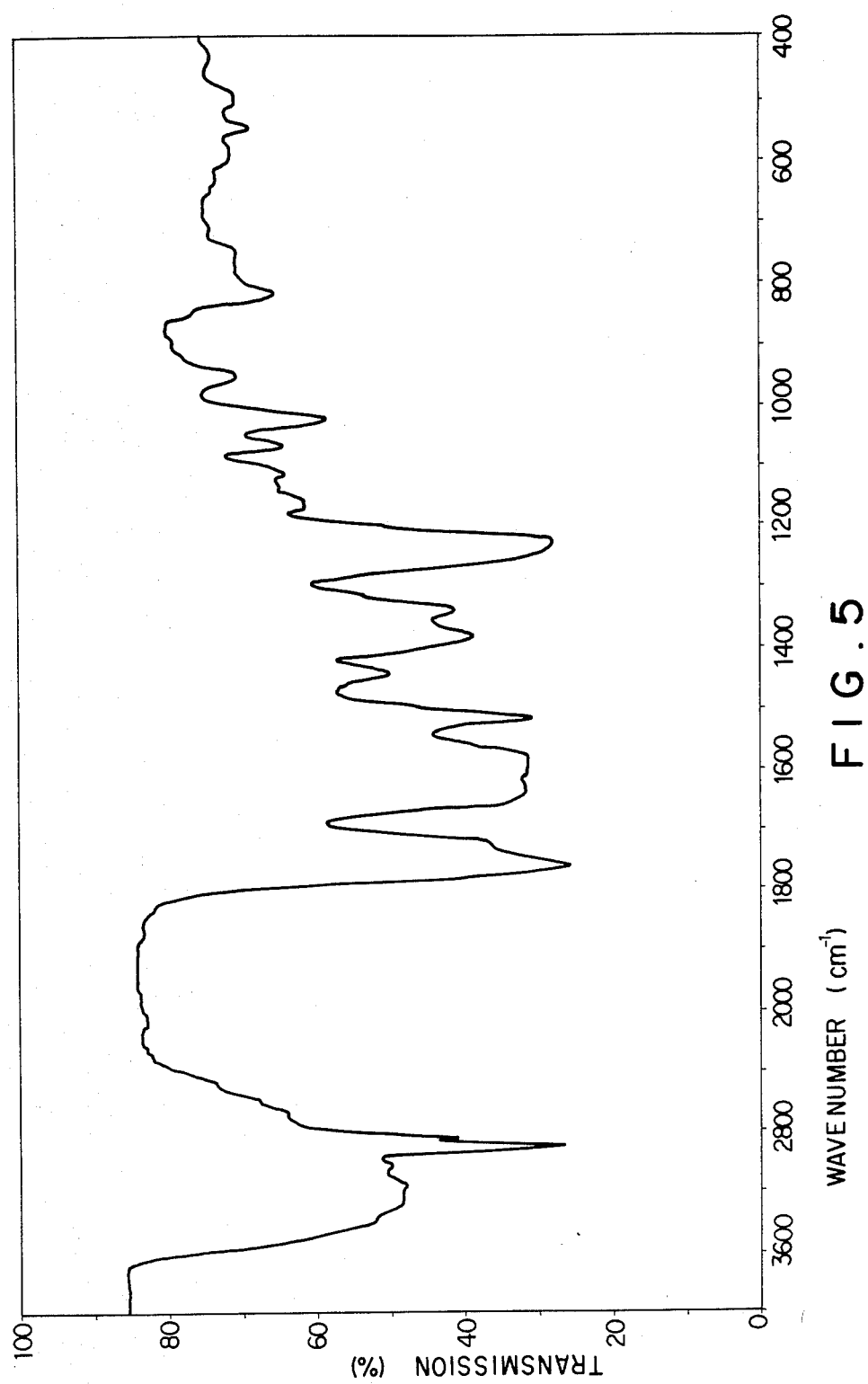

(3) infrared absorption bands (KBr method); $\nu_{max}$ (cm$^{-1}$): 2930, 1766, 1735, 1646, 1520, 1240. refer to FIG. 5.

(4) ultroviolet absorption bands in acetonitrile; $\lambda_{max}$ (nm): 223, 265.

TOXICOLOGICAL AND PHARMACOLOGICAL ACTIVITIES OF THE PRESENT COMPOUNDS

EXAMPLE 6

Acute toxicity of the present compounds were determined as follows.

Each of the present compounds was dispersed in a physiological saline solution. The dispersion was administered to an ICR-JCL mouse orally by a stomach sonde or intraperitoneally by injection at a predetermined amount.

After administration, the intoxication symptoms were continuously observed for a week and both survival and dead mice were autopsied to observe. LD$_{50}$ value was obtained from the cumulative mortality of the treated mice by applying the data to the Litchfield-Wilcoxon's graphical method. All of the present compounds gave LD$_{50}$ value of more than 10 g/kg in both oral and intraperitoneal administrations. The LD$_{50}$ value of cephalotin sodium as a comparative antibiotic is more than 5 g/kg.

These results show that the present compound is a safe substance having a low toxicity.

EXAMPLE 7

Effect of the present compounds on the intestinal bacterial colonies was examined.

Each of the present compounds was orally administered to mice (one group consisting of five female ICR mice of 6-week-old) for two consecutive days at a dose of 500 mg/kg/day.

Before and on the first day after the administration, feces of each mouse was collected and diluted with an anaerobic diluent (phosphoric buffer solution) of 100 times volume and ground. 0.1 ml of the diluted and ground feces was smeared on each culture medium shown in Table 1 and cultured aerobically or anaerobically (according to the anaerobic glove box method) under each condition shown in Table 1. The number of each bacterium shown in Table 1 was counted.

The results are shown in Table 2.

As seen from Table 2, the number of *Escherichia coli* showed no remarkable change as compared to that before administration in the case of each of the present compounds, while that number increased in the case of cephalotin as a comparative antibiotic. Further, the number of *Lactobacillus acidophilus* decreased in the case of cephalotin while such a decrease was not observed in the case of the present compound.

These results show that the present compounds do not affect the intestinal bacterial colonies in living bodies.

TABLE 1

Culture medium and culture condition of bacteria

| Bacterium | Culture medium | Culture condition |
|---|---|---|
| *Escherichia coli* | DHL agar | aerobic, 37° C., one day |
| *Pseudomonas aeruginosa* | NAC agar | aerobic, 37° C., one day |
| *Streptococcus* spp. | TATAC agar | aerobic, 37° C., one day |
| *Lactobacillus acidophilus* | LBS agar | anaerobic, 37° C., five days |
| *Lactobacillus bifidus* | BS agar | anaerobic, 37° C., five days |
| *Bacteroides* | NBGT agar | anaerobic, 37° C., five days |

TABLE 2

| Example No. | Logarithmic value of the number of bacterial cells per one gram of feces | | | | | |
|---|---|---|---|---|---|---|
| | E. coli | Ps. aeruginosa | Strept. spp. | L. acidophilus | L. bifidus | Bacteroides |
| 1 | 6.4 | <3.0 | 6.5 | 8.9 | 8.3 | 8.3 |
| 2 | 6.5 | <3.0 | 6.8 | 9.1 | 8.4 | 8.2 |
| 3 | 6.6 | <3.0 | 6.8 | 9.0 | 8.3 | 8.6 |
| 4 | 6.5 | <3.0 | 6.7 | 8.9 | 8.6 | 8.7 |
| 5 | 6.4 | <3.0 | 6.8 | 8.9 | 8.5 | 8.7 |
| Before administration | 6.4 | <3.0 | 6.8 | 9.0 | 8.4 | 8.3 |
| Cephalotin | 9.9 | <3.0 | 9.0 | 4.1 | 9.2 | 7.2 |

EXAMPLE 8

Antibacterial activity of the present compounds was examined as follows.

Antibacterial activity of each of the present compounds was examined against the following two bacteria according to the standard method of Japan Society of Chemotherapy:

*Escherichia coli* IFO 12734 and

*Staphylococcus aureus* IAM 1011

Each bacterial strain was inoculated into the Mueller-Hinton's culture medium and cultured at 37° C. for 18 to 48 hours. The culture medium was diluted so as to contain 1×10$^6$ cells of the bacteria per one ml, and the obtained medium was used as the bacterial specimen.

Agar plates were prepared by adding one part by weight of each solution of the present compounds having a predetermined concentration to nine parts by weight of Mueller-Hinton's culture medium.

A loopful amount of the bacterial specimen prepared above was smeared to make a streak of about 2 cm on each agar plate and cultured at 37° C. for 18 to 24 hours. The minimum concentration for completely inhibiting proliferation of the bacteria (referred to as MIC) was determined.

The results are shown in Table 3.

TABLE 3

| Example No. | MIC | |
|---|---|---|
| | E. coli | Staph. aureus |
| 1 | 50 | 0.78 |
| 2 | 100≦ | 3.13 |
| 3 | 100≦ | 100≦ |
| 4 | 100≦ | 100≦ |
| 5 | 100≦ | 1.56 |

EXAMPLE 9

The following experiment was carried out in order to prove that the present compound is activated in a living body.

As an enzyme for activating metabolism, a rat liver homogenate (S-9, manufactured by Oriental Yeast Company, Japan) was used in the following composition per one ml (hereinafter referred to as S-9 mix).

| | |
|---|---|
| S-9 | 0.5 ml |
| KCl | 3.3 mol |
| $MgCl_2.6H_2O$ | 8 μmol |
| Glucose-6-phosphate | 5 μmol |
| NADH | 4 μmol |
| NADPA | 4 μmol |
| 0.2 M phosphoric buffer solution (pH 7.4) | 0.5 ml |

0.1 ml of each solution of the present compounds at a concentration of various value was mixed with 0.9 ml of S-9 mix or 0.9 ml of 0.1M phosphoric buffer solution (as a control) and the obtained mixture was incubated at 37° C. for 20 min with shaking.

*Staphylococcus aureaus* IAM 1011 was inoculated into a Mueller-Hinton's culture medium and cultured at 37° C. for 18 hours. The culture medium was adjusted to a cell concentration of $1 \times 10^8$ per one ml and mixed with 50 times by volume of Mueller-Hinton's agar culture medium to obtain an agar plate.

A penicillin cup of 8 mm in diameter was placed on the agar plate prepared above, and into the cup 0.1 ml of the mixture was introduced and allowed to stand at 4° C. for 2 hours and then cultured at 37° C. for 18 hours to measure the diameter of a circle in which the proliferation of bacteria was inhibited (proliferation-inhibiting circle). The results are shown in Table 4. In Table 4, the proliferation-inhibiting index is shown with the ratio (%) of the diameter of the proliferation-inhibiting circle obtained by using each of the present compounds to that obtained by using the comparative compound.

| Index | % |
|---|---|
| − | 0 |
| ± | 0–1 |
| + | 1–33 |
| ++ | 33–66 |
| +++ | 66–100 |

TABLE 4

| | Proliferation-inhibiting index (%) | |
|---|---|---|
| Example No. | Before adding S-9 mix | After adding S-9 mix |
| 3 | − | + |
| 4 | − | + |
| 5 | + | +++ |

As seen from Table 4, the antibacterial activity of the present compound is activated by an enzyme in a living body, although it itself shows a low antibacterial activity in the absence of an activating enzyme.

EXAMPLE 10

Effect of the present compounds on the infection was examined.

*Escherichia coli* IFO 12734 ($1.4 \times 10^8$) was inoculated intraperitoneally to ddY-SPF mice (a group consisting of 20 mice). Just after and at 4 hours after the infection, each of the present compounds was administered orally at a dose of 500 mg/kg and the mortality of the mice due to the infection was observed for 7 days. More than 35% of the mice administered with the present compound survived even on the 7th day after the infection, while all mice without the administration with the present compound died on the 2nd day after infection.

The results show that the present compound is an effective medicine for oral administration against an infectious disease.

MANUFACTURE OF THE PHARMACEUTICAL PREPARATIONS

EXAMPLE 11

(1) Tablet

A tablet was prepared by a following composition in one tablet of 200 mg:

| | |
|---|---|
| the present compound of Example 4 | 175 mg |
| lactose | 16 mg |
| starch | 5 mg |
| hydroxypropylcellulose | 3 mg |
| magnesium stearate | 1 mg |

The present compound and lactose were mixed and then an aqueous solution of hydroxypropylcellulose was admixed, and the mixture was kneaded, dried and pulverized. Then magnesium stearate dispersed previously into starch was admixed and the mixture was made into a tablet by the conventional method for tabletting.

(2) Granule

A granule was prepared by a following composition;

| | |
|---|---|
| the present invention of Example 5 | 176 mg |
| lactose | 16 mg |
| starch | 4 mg |
| hydroxypropylcellulose | 4 mg |

The present compound, starch and lactose were mixed, and an aqueous solution of hydroxypropylcellulose was admixed and the mixture was dried and pulverized. The pulverized material was sifted by 12 to 48 mesh sieves to obtain a granule.

What is claimed is:

1. A cephalosporin derivative having the formula (I):

$$R_1-CONH-\underset{O}{\overset{S}{\underset{N}{\bigsqcup}}}-CH_2OCOCH_3 \quad (I)$$
$$\qquad\qquad COR_2$$

wherein $R_1$ is adamantyl–$CH_2-$ and $R_2$ is

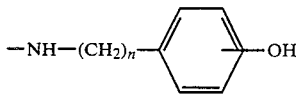

wherein n is 0, 1 or 2;

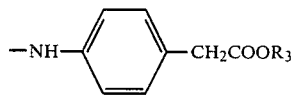

wherein $R_3$ is a hydrogen atom, an alkyl group having 1 to 4 carbon atoms or an alkali metal.

2. The derivative of claim 1, which is N-(4-carbomethoxymethylphenyl)-7-(adamantane-1-acetamido)cephalosporanamide.

3. The derivative of claim 1, which is N-(4-hydroxyphenyl)-7-(adamantane-1-acetamido)cephalosporanamide.

4. The derivative of claim 1, which is N-[beta-(4-hydroxyphenyl)ethyl]-7-(adamantane-1-acetamido)-cephalosporanamide.

5. An antibacterial composition in dosage unit form comprising as an active ingredient an effective dosage of a cephalosporin derivative having the formula (I):

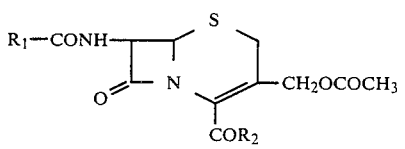

wherein $R_1$ is

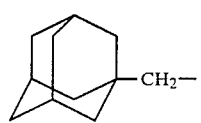

and $R_2$ is

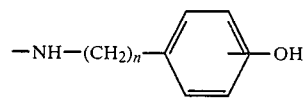

wherein n is 0, 1 or 2;

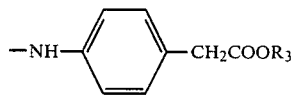

wherein $R_3$ is a hydrogen atom, an alkyl group having 1 to 4 carbon atoms or an alkali metal and a pharmaceutically acceptable carrier therefor.

6. The antibacterial composition of claim 5, wherein the derivative N-(4-carbomethoxymethylphenyl)-7-(adamantane-1-acetamido)cephalosporanamide.

7. The antibacterial composition of claim 5, wherein the derivative is N-(4-hydroxyphenyl)-7-(adamantane-1-acetamido)cephalosporanamide.

8. The antibacterial composition of claim 5, wherein the derivative is N-[beta-(4-hydroxyphenyl)ethyl]-7-(adamantane-1-acetamido)cephalosporanamide.

* * * * *